US010791841B2

(12) United States Patent
Seo

(10) Patent No.: US 10,791,841 B2
(45) Date of Patent: Oct. 6, 2020

(54) LUMBAR SUPPORT CHAIR HAVING STRUCTURE ADJUSTABLE ACCORDING TO CHANGE OF POSTURE

(71) Applicant: Jun Seok Seo, Incheon (KR)

(72) Inventor: Jun Seok Seo, Incheon (KR)

(73) Assignee: Jun Seok Seo, Incheon (KR)

( * ) Notice: Subject to any disclaimer, the term of this patent is extended or adjusted under 35 U.S.C. 154(b) by 0 days.

(21) Appl. No.: 16/464,964

(22) PCT Filed: Nov. 28, 2017

(86) PCT No.: PCT/KR2017/013698
§ 371 (c)(1),
(2) Date: May 29, 2019

(87) PCT Pub. No.: WO2018/101704
PCT Pub. Date: Jun. 7, 2018

(65) Prior Publication Data
US 2020/0022497 A1     Jan. 23, 2020

(30) Foreign Application Priority Data

Nov. 29, 2016   (KR) .......................... 10-2016-0159933

(51) Int. Cl.
*A47C 7/42*     (2006.01)
*A47C 7/02*     (2006.01)
*A47C 7/46*     (2006.01)
*A47C 7/40*     (2006.01)

(52) U.S. Cl.
CPC .............. *A47C 7/425* (2013.01); *A47C 7/021* (2013.01); *A47C 7/029* (2018.08); *A47C 7/407* (2013.01); *A47C 7/46* (2013.01)

(58) Field of Classification Search
CPC ......... A47C 3/029; A47C 7/425; A47C 7/021; A47C 7/46; A47C 7/407; A47C 7/029
USPC ................ 297/258.1, 378.1, 452.21, 215.12
See application file for complete search history.

(56) References Cited

U.S. PATENT DOCUMENTS

| 1,309,725 | A | * | 7/1919 | Gerstenmaier et al. ..................... A61G 5/1045 297/452.25 |
| 2,967,565 | A | * | 1/1961 | Schultz .................... A47C 3/12 297/239 |
| 3,712,670 | A | * | 1/1973 | Svehla ....................... B62J 1/00 297/214 |
| 4,521,052 | A | * | 6/1985 | Cone ...................... A47D 1/103 297/3 |

(Continued)

FOREIGN PATENT DOCUMENTS

| JP | 2011-254878 A | 12/2011 |
| KR | 10-1045677 B1 | 6/2011 |

(Continued)

OTHER PUBLICATIONS

International Search Report from corresponding PCT Application No. PCT/KR2017/013698, dated Feb. 26, 2018.

*Primary Examiner* — Milton Nelson, Jr.
(74) *Attorney, Agent, or Firm* — Harness, Dickey & Pierce, P.L.C.

(57) ABSTRACT

The present invention relates to a chair and, more particularly, to a lumbar support chair of which the shape and position are adjusted according to a change of posture of a sitter to support a user's lumbar, thereby providing a comfortable feeling and a posture correction effect.

5 Claims, 10 Drawing Sheets

(56) References Cited

U.S. PATENT DOCUMENTS 5,820,220 A * 10/1998 Wu .................. A47C 7/407
                                                        297/378.1
8,960,799 B2 * 2/2015 Yoon .................. A47C 1/146
                                                        297/378.1

FOREIGN PATENT DOCUMENTS

| KR | 10-2011-0117193 A | 10/2011 |
| KR | 10-2015-0009835 A | 1/2015 |
| KR | 10-2016-0091930 A | 8/2016 |

* cited by examiner

LUMBAR SUPPORT CHAIR HAVING STRUCTURE ADJUSTABLE ACCORDING TO CHANGE OF POSTURE

CROSS-REFERENCE TO RELATED APPLICATIONS

This application is a national phase application of PCT Application No. PCT/KR2017/013698, filed on 28 Nov. 2017, which claims priority to Korean Patent Application No. 10-2016-0159933, filed on 29 Nov. 2016. The entire disclosure of the applications identified in this paragraph is incorporated herein by references.

FIELD

The present invention relates generally to a chair and, more particularly, to a lumbar support chair of which the shape and position are adjusted according to a change in posture of a sitter so as to support the sitter's body when the chair is seated directly on a general chair, a sofa, a car seat, or a floor, thereby providing a comfortable feeling and a posture correction effect.

BACKGROUND

Generally, a chair is an item to assist a sitter in relaxing or in working while sitting thereon for a long time. A general chair comprises a seat which supports the sitter's buttocks and thighs thereon, and a back support which supports the sitter's waist and back. However, in case of the general chair, as the positions of the seat and back support are fixed throughout the use thereof, the back support could not satisfactorily support the sitter's back and waist if the sitter changes his/her posture by leaning his/her waist and back forward or crosses his/her legs, or if the sitter leans his/her body to one side, etc., causing the sitter to feel uncomfortable. Also, as the sitter's posture is improper, there has been a problem in accompanying deformation of the sitter's body shape.

In order to solve these problems such as inconvenience caused by the change of the sitter's posture and deformation of the sitter's body shape, Korean Patent No. 10-1489702 suggests a method and an apparatus for dynamically correcting posture. According to this patent, an orthopedic device is configured to take a bowl shape so as to support a user's buttocks and thighs, and a lower part of the user's waist, the device being made of a synthetic material having an elasticity which serves to elastically transform the shape thereof according to a change in the sitter's posture. However, as the orthopedic device according to this patent is generally formed in a cushion type so as to mainly support the user's buttocks and thighs, the device could not effectively support the sitter's waist or back, failing to provide a convenient feeling in seating when the sitter leans backward to take a rest. In addition, as the device is usually formed of a synthetic resin which is thin and easily elastically transformable, any force applied to the device according to a change of posture causes the shape thereof to be easily transformed. In this regard, this patent rather has a defect that cannot firmly support the sitter's body portions.

In the meantime, Korean Patent No. 10-1598473 suggests a chair in which a seat and a back support are integrally combined, thereby being capable of providing comfort and inducing correct posture while a sitter is sitting on the chair. As the chair according to this patent has a back support, the chair is advantageous in that the sitter's back and waist can be effectively supported. However, as the seat and the back support are entirely made of rigid plastic materials, the entire chair is transformed in shape and changed in position simultaneously even when force is locally applied only to a partial area of the chair, that is, when a part of the sitter's body is leaned to one side. As the chair cannot match the sitter's posture, there is a defect that the chair causes the sitter to feel uncomfortable.

SUMMARY

Technical Problem

Accordingly, the present invention has been made keeping in mind the above problems occurring in the related art and is directed to solving the defects of the general chairs as described above. In this regard, an objective of the present invention is to provide a chair being capable of effectively supporting a sitter's back and waist even when the sitter's posture is changed, thereby bringing a comfortable feeling and a posture correction effect, and in particular, the chair whose shape and position are changed to an optimized shape and position adaptively to the sitter's posture, enabling the sitter to feel comfortable in any posture.

Technical Solution

In order to accomplish the above objectives, the present invention provides a lumbar support chair the shape of which can be adjusted according to a sitter's posture, wherein the seat is configured to take a bowl shape having a center that is concavely curved and a bottom portion that is extended upwardly from the center toward the outside in an arc shape, and a cut portion is formed in the seat (10), the cut portion halving the seat into a left part and a right part from a front end toward a rear end of the seat.

Preferably, the seat is configured to have a front end edge which is rounded in a downward direction, and the seat is also configured to have a thickness which becomes thinner from a front side toward a rear side thereof.

Preferably, the back support is hingedly coupled to the rear end of the seat so as to be foldable, a first uneven part and a second uneven part which are coupled as a pair are both formed on left and right sides of a rear end part of the seat and a lower end part of the back support respectively, and the first uneven part and the second uneven part are coupled with each other by a hinge pin which penetrates the first uneven part and the second uneven part, and a stopper bar is provided on a rear end side of the first uneven part of the seat, to support the back support so as to prevent the back support from being further tilted rearward.

Preferably, the stopper bar is horizontally extended so as to be coupled to respective convex parts of the first uneven part simultaneously and faces a part of the back support just above an upper part of the second uneven part.

Advantageous Effects

According to a chair of the present invention, a sitter's back and waist can be effectively supported even when the sitter's posture is changed, thereby bringing comfort and posture correction effects, and in particular, the chair whose shape and position are changed to an optimized shape and position adaptively to the sitter's posture, thereby enabling the sitter to feel comfortable in any posture. Also, the chair according to the present invention is available to be used on all types of chairs including general chairs, sofas, car seats, etc. for office or home use, or used in a sedentary type on inner floors or outdoor grounds. In addition, as the back support is configured to be foldable, the chair according to the present invention is advantageous in terms of easy storage and transportation.

DESCRIPTION OF THE SYMBOLS

Figure 1:
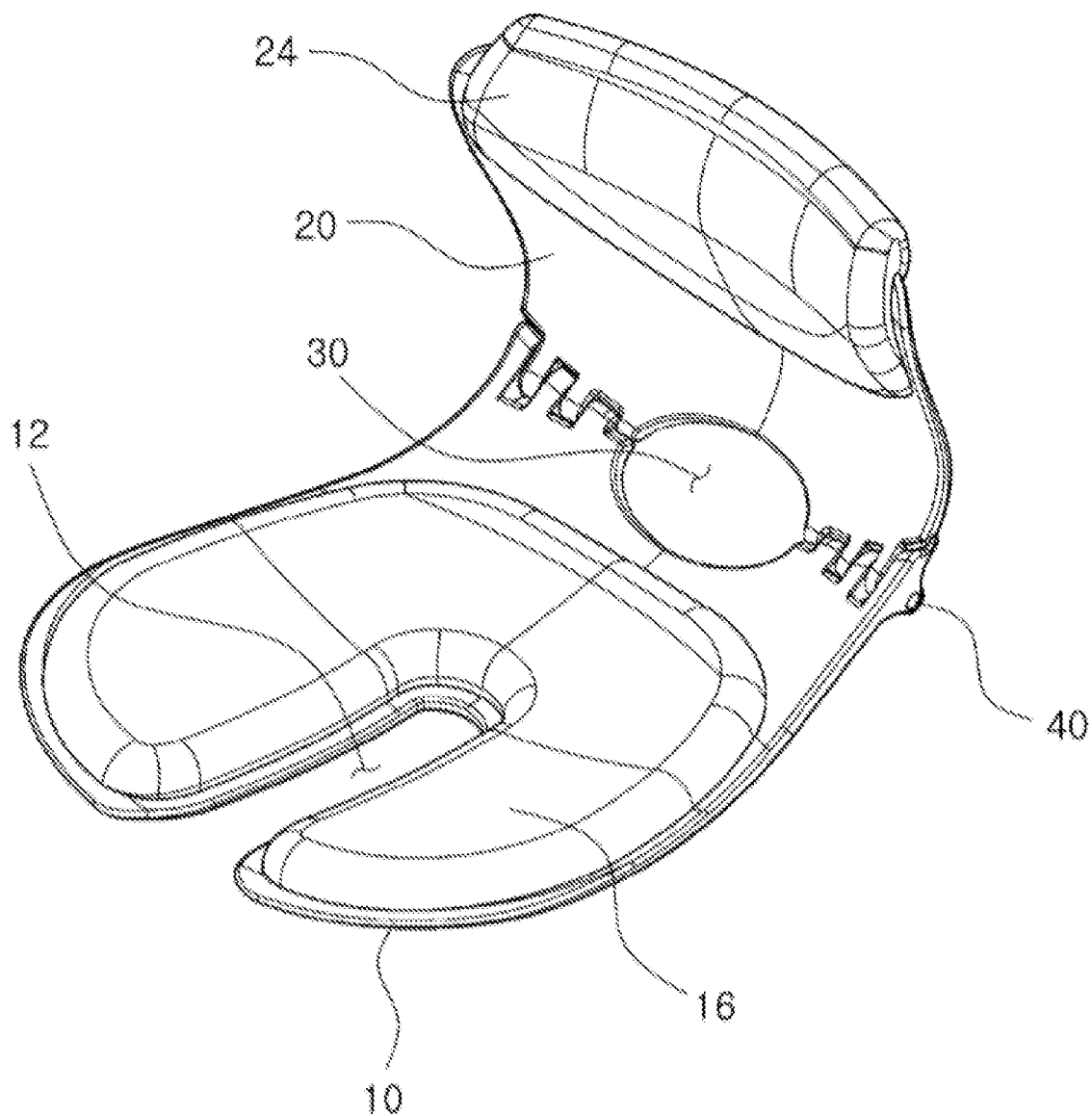
FIG. 1 is a prospective view showing a front of a chair according to an embodiment of the present invention.

| 10: Seat | 12: Cut part |
|---|---|
| 14: First uneven part | 18: Stopper bar |
| 20: Back support | 22: Second uneven part |
| 30: Gripping hole | |

DETAILED DESCRIPTION

Hereinbelow, configurations and operations of the lumbar support chair according to exemplary embodiments of the present invention will be described in detail with reference to the accompanying drawings.

As shown in FIGS. 1 to 4, a lumbar support chair according to the present invention comprises a seat 10 and a back support 20.

The seat 10 supports a sitter's buttocks and thighs thereon. The seat 10 is made of synthetic resin materials which are generally rigid but somewhat elastic. As shown in the drawings, a central portion thereof is concave and slightly extended upwardly toward the outside in an arc shape, so that it can correspond to the sitter's body shape, taking a bowl shape. Owing to this shape, the sitter's buttocks and thighs can be stably seated thereon.

Also, due to the bowl shape of the central portion, the bottom portion of the seat 10 is upwardly extended toward the outside from the center thereof in an arc shape. In this regard, if a force is applied to any one side of the seat 10 from the upper thereof, tilting (rotation) becomes available on the basis of the central position as a support point. Effects resulting from this operation will be described later in more details.

A cut portion 12 is formed in the seat 10, and the cut portion 12 is extended from a front end thereof as much as a predetermined length toward the rear of the seat 10. The cut portion 12 halves the front end portion of the seat 10 into a left part and a right part. The halved parts are configured to support the sitter's left and right thighs respectively, and to be transformed independently of each other when the sitter's posture is changed.

As another configuration, it is preferable that the seat 10 is configured to have a front end edge rounded downwardly, so as to prevent the sitter's thighs from getting poked or being pressed. As described below, it is also preferable to configure the halved parts to become thinner toward the rear side from the front side of the seat 10 so that they can be smoothly elastically transformed when the sitter's posture is changed. Also preferably, a cushion 16 is formed on the surface of the seat in a detachable manner.

Figure 2:
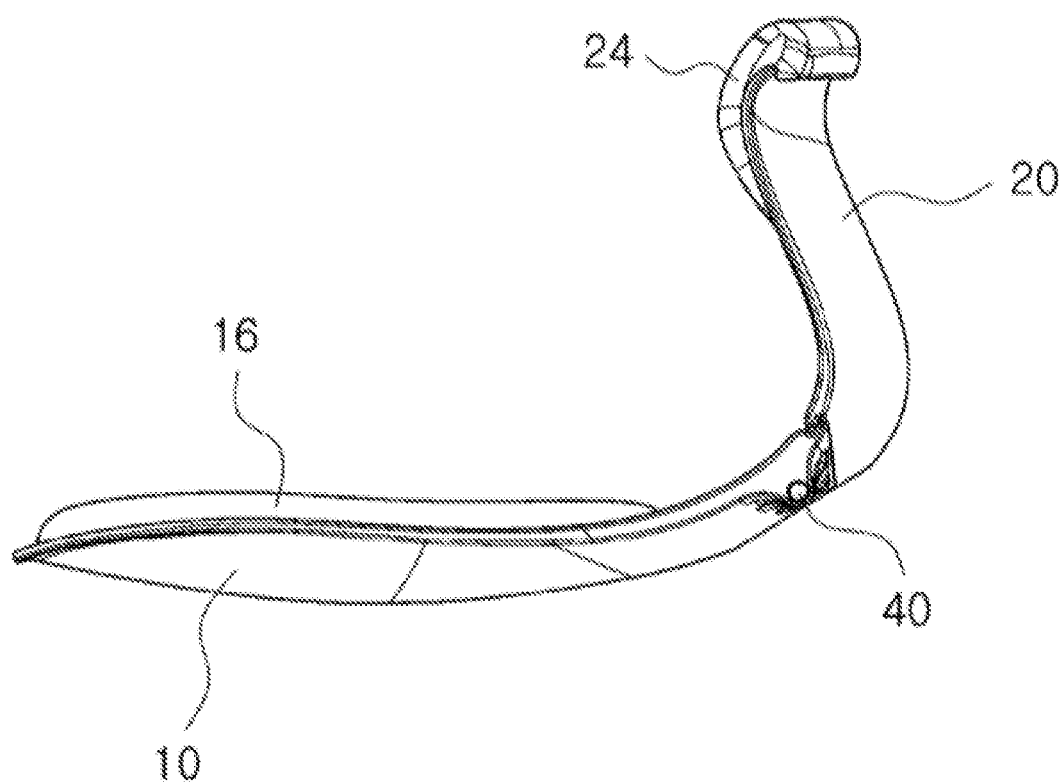
FIG. 2 is a side elevational view showing of the chair according to an embodiment of the present invention.
Figure 3:
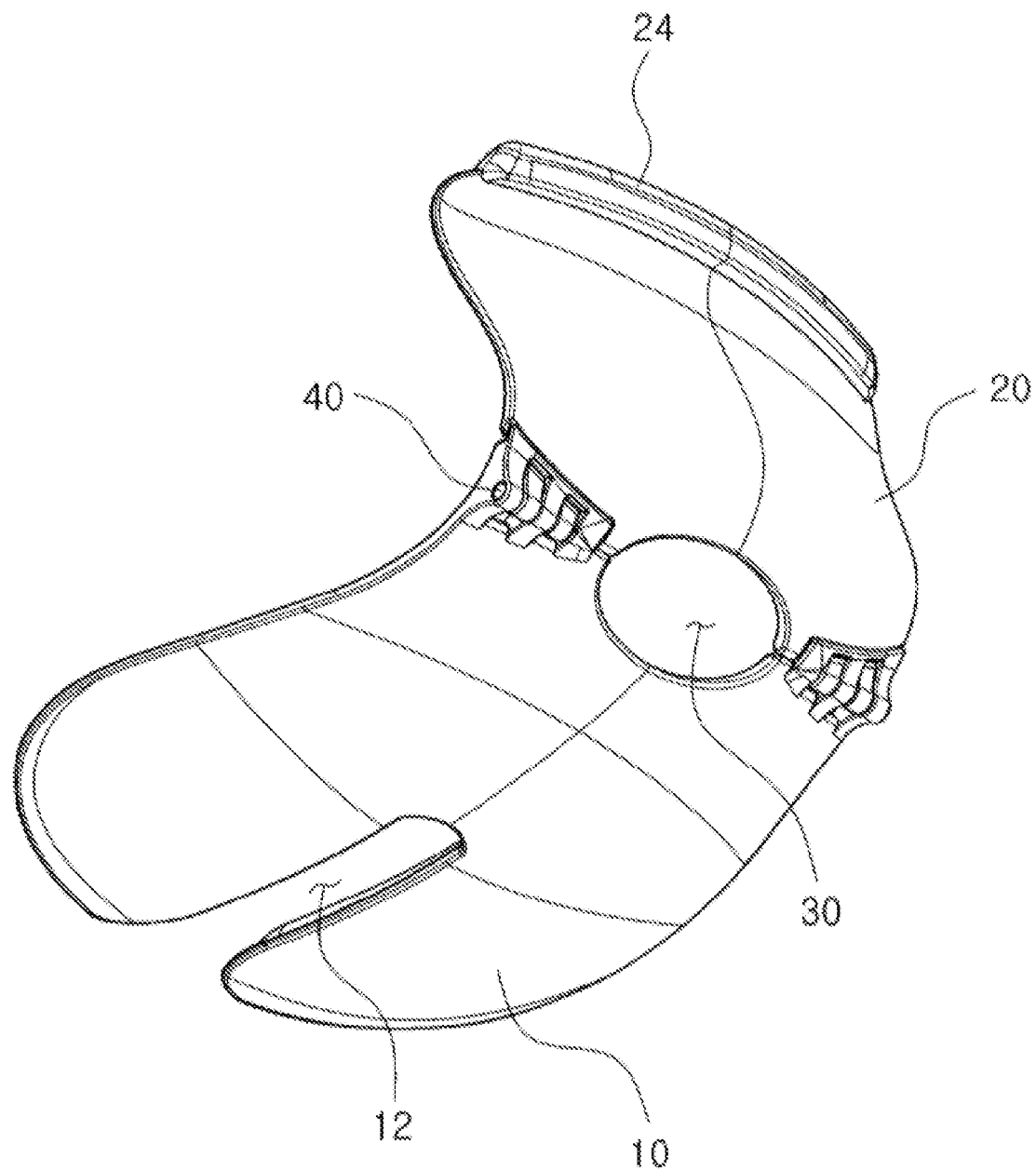
FIG. 3 is a perspective view showing a rear of the chair according to an embodiment of the present invention.

The back support 20 is a portion to be coupled to the rear end portion of the seat 10, supporting the sitter's waist and back. As shown in FIG. 2, the back support 20 is formed curvedly to match the sitter's buttocks and waist shape, and the upper portion of the back support 20 is smoothly bent toward the rear side thereof forming an arc shape, so that the sitter can be conveniently and stably supported even when the sitter leans his/her waist backwardly. In this regard, it is preferable that the back support as a whole takes an S shape.

In order to firmly support the sitter's waist and at the same time make the back support 20 easily adjusted in shape to match the sitter's changed posture when the sitter leans his/her waist back, it is preferable that the lower part of the back support 20 is slightly heavier and becomes thinner as it is close to the upper thereof. As shown in FIG. 1, it is also preferable that a cushion 24 is formed in a detachable manner on the upper front portion thereof.

Figure 4:
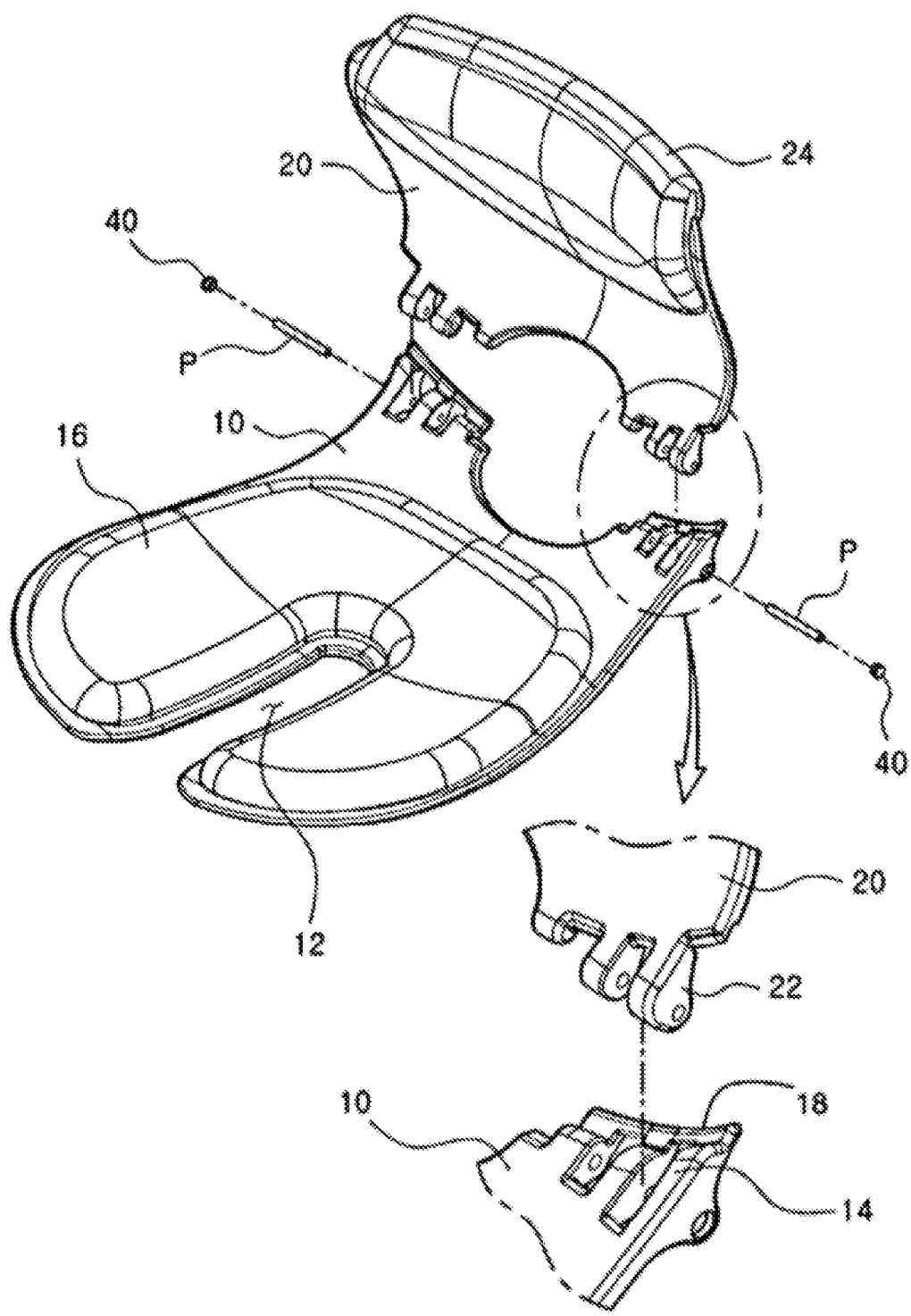
FIG. 4 is an exploded view of the chair according to an embodiment of the present invention.
Figure 5:
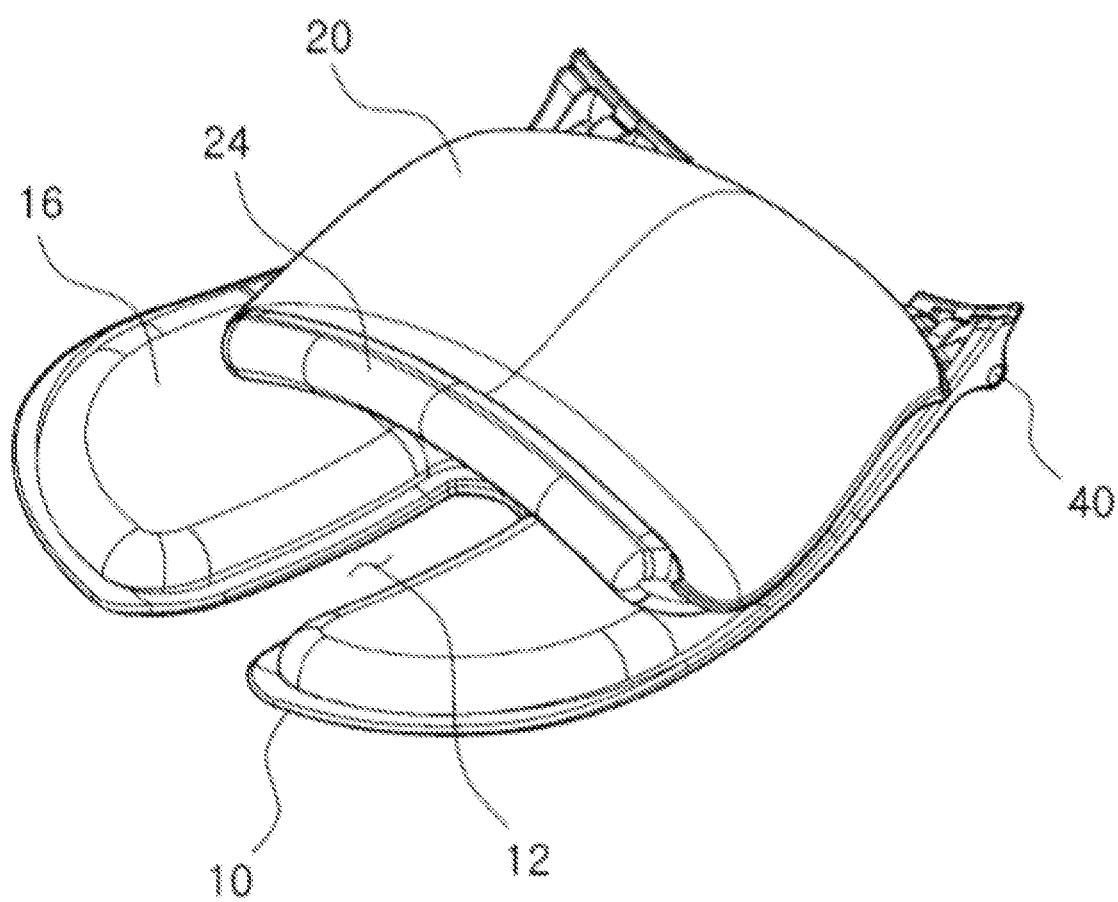
FIG. 5 is a view showing a folded state of the chair according to an embodiment of the present invention.

The back support 20 is preferably configured to be hingedly coupled to the rear end portion of the seat 10 so as to be foldable, to facilitate storage and transportation. For this, as shown in FIG. 4, a first uneven part 14 and a second uneven part 22 that are coupled as a pair are both formed on left and right sides of the rear end portion of the seat 10 and the lower end portion of the back support 20 respectively, to which a hinge pin (P) penetrating the first uneven part 14 and the second uneven part 22 is coupled. The hinge pin P is configured to be closed by a cap 40 in the outside so as not to be exposed to the outside. Accordingly, the back support 20 rotates around the hinge pin P, and as shown in FIG. 5, the back support 20 is foldable, thereby being capable of minimizing its volume in storage and transportation.

Additionally, a gripping hole 30 is formed on the coupling portion of the seat 10 and the back support 20, so that a user can grip the seat 10 so as to easily transport the chair.

Meanwhile, where the seat 10 and the back support 20 are coupled hingedly, the back support 20 may be liable to be tilted backward as the back support 20 cannot receive strength when the sitter leans his/her waist and back against the back support 120. To prevent this liability, a stopper bar 18 is formed on the rear end side of the first uneven part 14 of the seat 10, as shown in FIG. 4. The stopper bar 18 is horizontally extended and coupled simultaneously to respective convex (projected) parts of the first uneven part 14, facing a part of the back support 10 just above an upper part of the second uneven part 22 and supporting the back support 20 to prevent the back support 20 from being further tilted rearward. Accordingly, the back support 20 can firmly support the sitter's waist and back.

The lumbar support chair of the present invention has been described above in terms of configuration. Hereinafter, uses and operations of the chair of the present invention will be described below.

Figure 6:
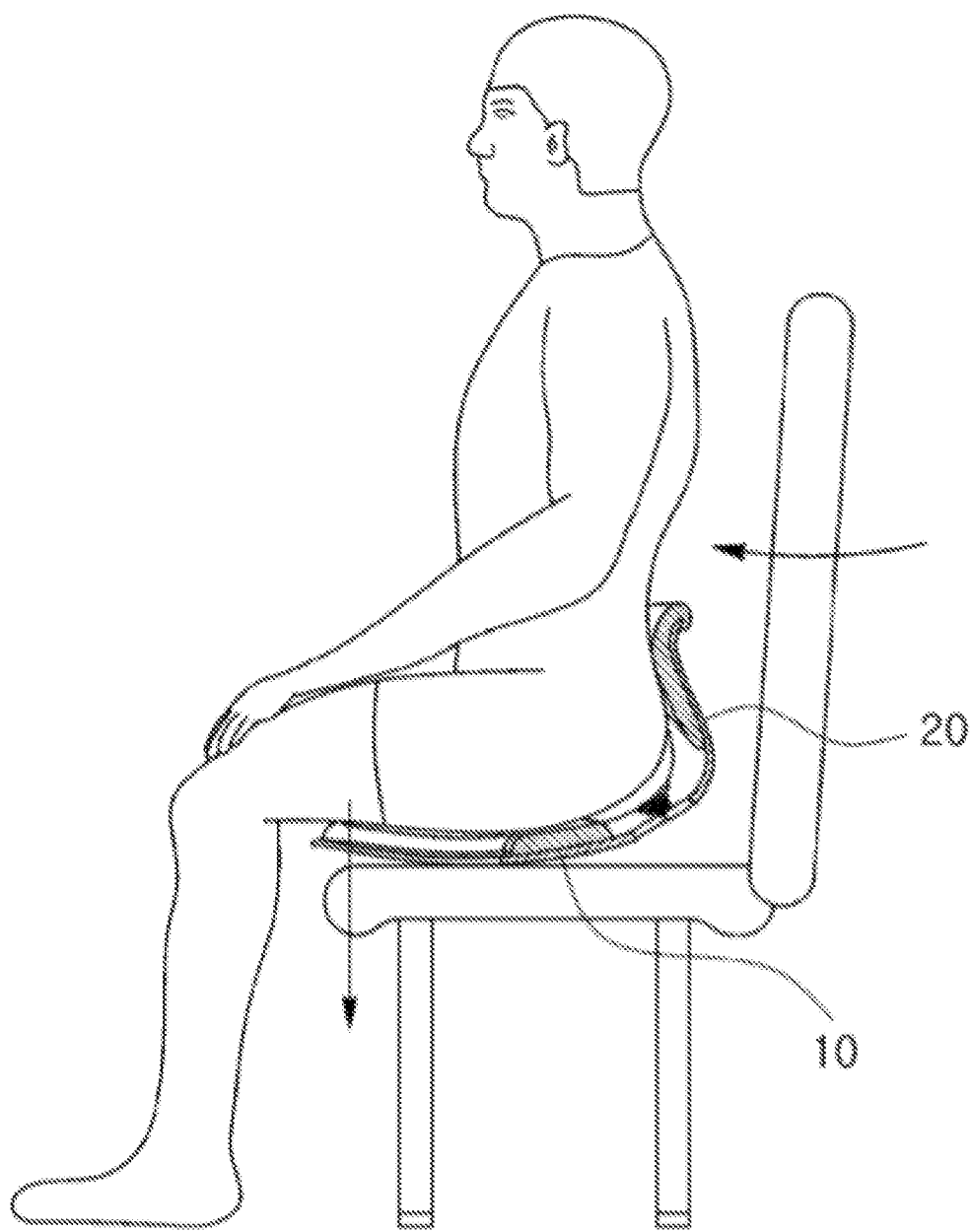
FIG. 6 is a view showing a sitter who sits in a proper posture on the chair according to an embodiment of the present invention.

FIG. 6 shows a sitter who sits in a proper posture on the chair according to an embodiment of the present invention. As shown therein, the sitter can sit on the chair of the present invention which is seated on a general chair. Furthermore, the chair of the present invention can be directly put on floors, wood floors, or on the ground while camping. In all use types of the chair as enumerated above, operations of the chair of the present invention would be of the same.

Referring to FIG. 6, where the sitter sits on the chair of the present invention in a proper posture, a load is applied to the front end side of the seat 10 by the sitter's thighs, the chair in its entirety is tilted toward the front side of the seat on the basis of the bottom surface of the seat 10, to thereby allow the back support 20 to support the sitter's waist and back.

Figure 7:
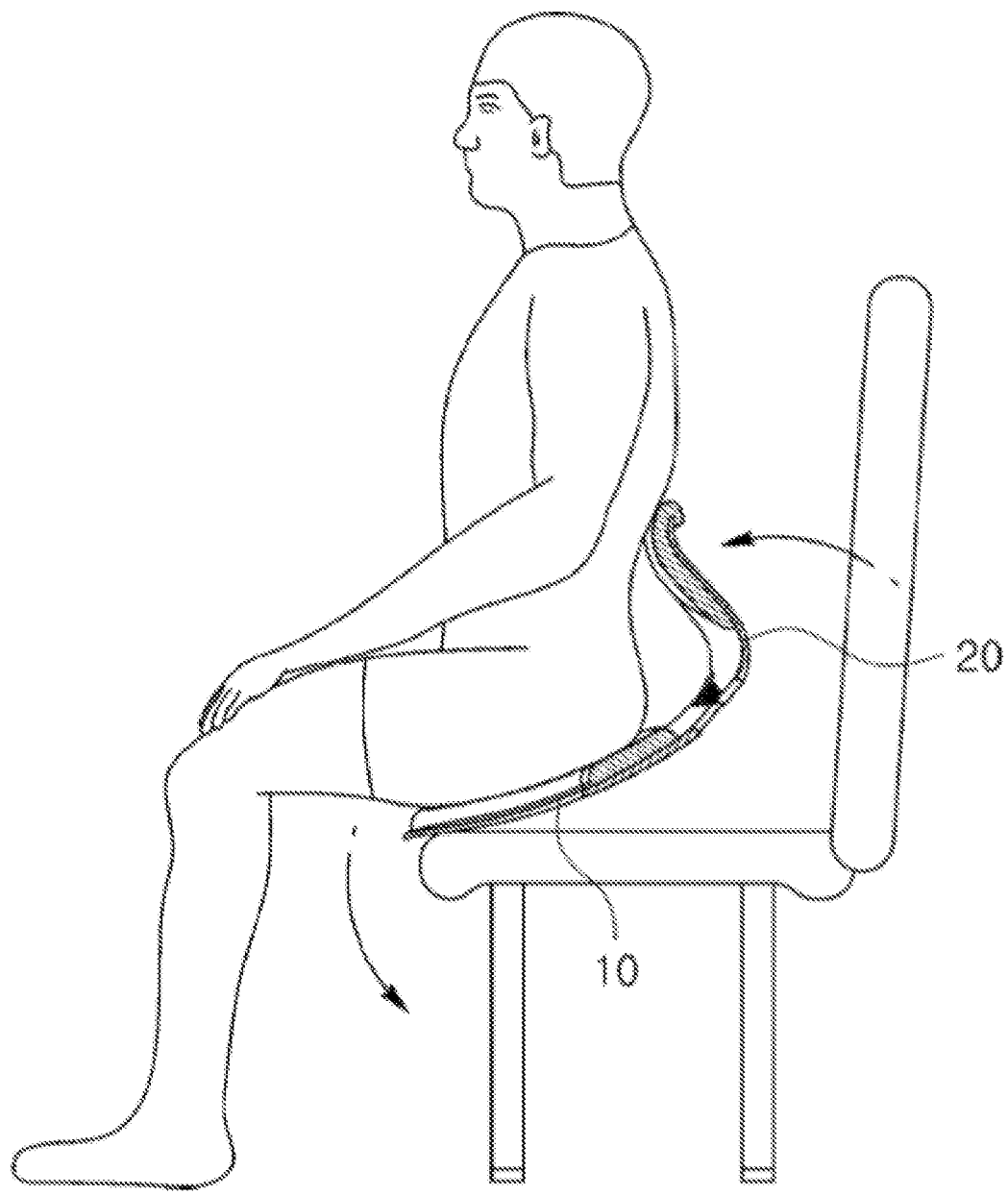
FIG. 7 is a view showing the sitter who sits on a front end of a seat of the chair according to an embodiment of the present invention.

Also, as shown in FIG. 7, even where the sitter bends his/her body forward or sits on the front end of the seat 10, the chair is tilted as a whole, thereby supporting the sitter's waist and back portions. As described above, when the chair of the present invention is used together with a general chair, the sitter's waist and back can be supported by the chair of the present invention even when the sitter's body is separated from the general chair, providing comfort to the sitter. Also, as the sitter can lean his back comfortably, the sitter can also enjoy a posture correction effect.

Figure 8A:
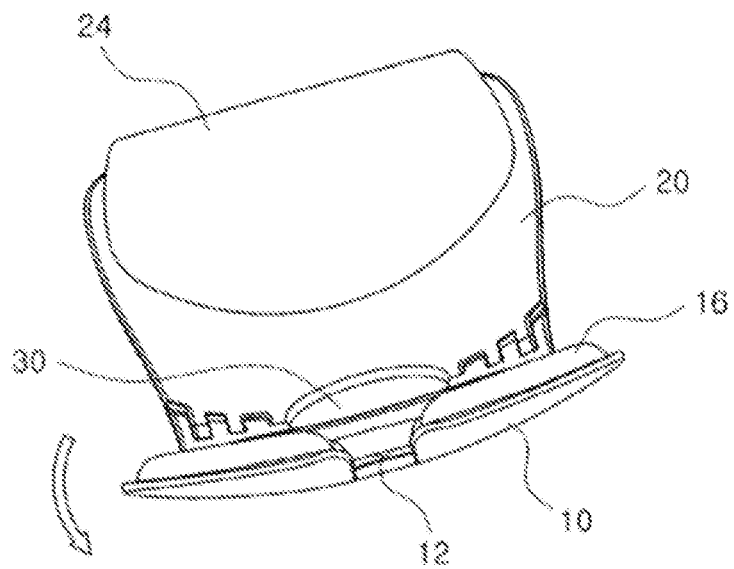
FIGS. 8A and 8B are views showing rightward and leftward tilting of the chair according to an embodiment of the present invention according to a posture of the sitter.
Figure 8B:
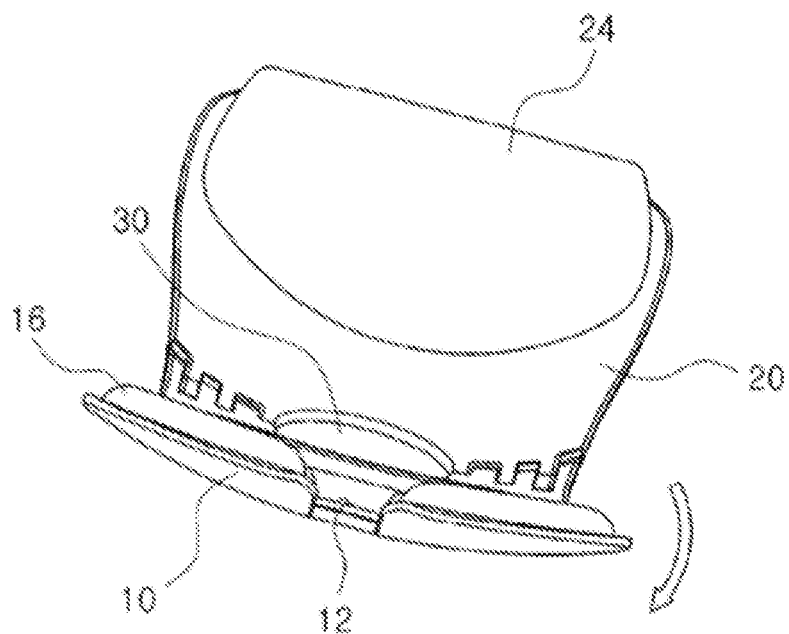
Figure 9A:
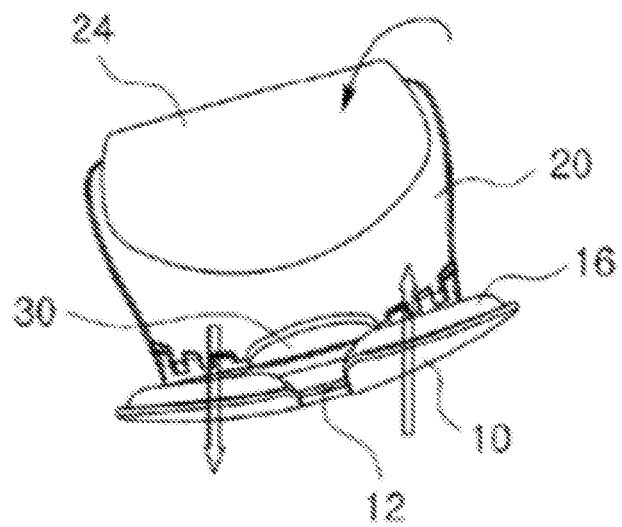
FIGS. 9A, 9B and 9C are views showing shapes of the seat of the chair according to an embodiment of the present invention, which are changed according to the sitter's posture.
Figure 9B:
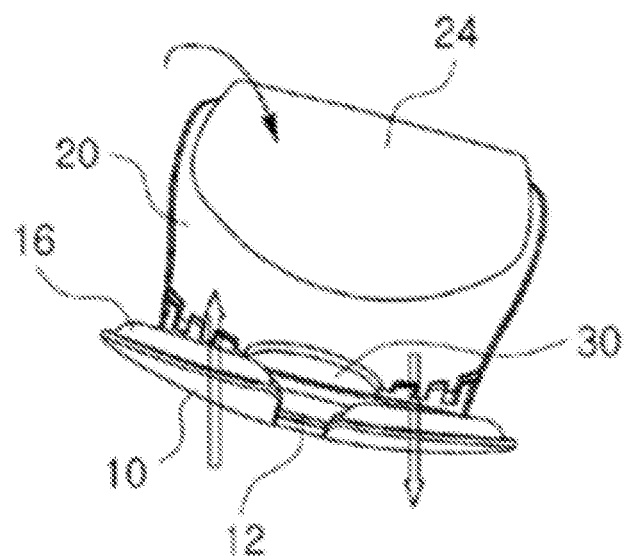
Figure 9C:
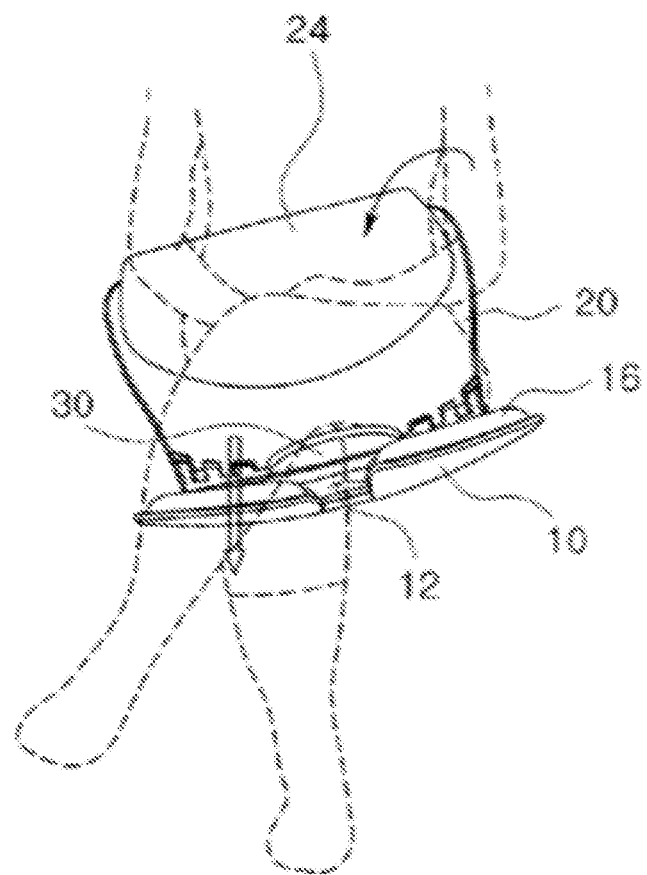

FIGS. 8 and 9 show shapes and positions of the chair of the present invention changed according to changes in various postures of the sitter.

As shown in FIG. 8, where a load is applied only to one side of the seat 10 as the sitter leans his/her body to any one side, the chair is as a whole tilted on the basis of the bottom surface of the seat 10. Accordingly, even though the sitter changes his/her posture, the position of chair is changed adaptively to this change, to support the sitter's waist and back.

Also as shown in FIG. 9, where a load is applied to only one part of the seat 10 which is halved by a cut portion if the sitter moves his/here body to a front side or lifts one of his/her thighs, the one part of the seat 10 to which the load is applied is adjusted downwardly, causing one side portion of the back support 20 in a diagonal direction to be tilted forwardly according to the principle of levers, thus supporting the sitter's waist and back. In the meantime, the other portion of the seat 10 to which no load is applied is tilted upwardly, so as to continuously support the lifted thigh portion.

As shown in (c) of FIG. 9, where the sitter puts one of his/her legs on the other leg or crosses his/her legs, thereby applying different loads to both sides of a halved seat 10, both sides of the halved seat 10 are independently transformed, being capable of effectively supporting the sitter's waist and back adaptively to the sitter's posture.

Exemplary embodiments of the present invention have been described in details. In this regard, the scope and spirit of the present invention will not be limited to the exemplary embodiments of the present invention described above, and those skilled in the art will appreciate that various modifications, additions and substitutions are possible, without departing from the scope and spirit of the invention as disclosed in the accompanying claims.

Accordingly, as the exemplary embodiments of the present invention have been provided to fully inform the category of the invention to those skilled in the art, it should be appreciated that they are all for illustrative purposes and the present invention shall only be interpreted on the basis of the category of the claims.

What is claimed is:

1. A lumbar support chair having a seat and a back support, wherein the seat is configured to take a bowl shape having a center that is concavely curved and a bottom portion that is extended upwardly from the center toward an outside of the seat in an arc shape, and a cut portion is formed in the seat, the cut portion halving the seat into a left part and a right part from a front end toward a rear end of the seat, wherein a first uneven part and a second uneven part are formed on both left and right sides of a rear end part of the seat and a lower end part of the back support, respectively, wherein a stopper bar is provided on a rear end side of the first uneven part of the seat, to support the back support so as to prevent the back support from being further tilted rearward, and wherein the stopper bar is horizontally extended so as to be coupled to respective convex parts of the first uneven part simultaneously and faces a part of the back support just above an upper part of the second uneven part.

2. The lumbar support chair of claim 1, wherein the seat is configured to have a front end edge which is rounded downward in a downward direction.

3. The lumbar support chair of claim 1, wherein the seat is configured to have a thickness which becomes thinner from a front side toward a rear side thereof.

4. The lumbar support chair of claim 1, wherein the back support is hingedly coupled to the rear end of the seat so as to be foldable.

5. The lumbar support chair of claim 4, wherein the first uneven part and the second uneven part are coupled as a pair and the first uneven part and the second uneven part are coupled with each other by a hinge pin which penetrates the first uneven part and the second uneven part.

* * * * *